(12) United States Patent
High, Jr. et al.

(10) Patent No.: US 11,717,093 B2
(45) Date of Patent: Aug. 8, 2023

(54) MODIFIED AND IMPROVED SELF-SANITIZING CHAIR

(71) Applicants: Zeb F. High, Jr., Wilson, NC (US); Isiah Joseph, Virginia Beach, VA (US); Gary Gordon, Suffolk, VA (US)

(72) Inventors: Zeb F. High, Jr., Wilson, NC (US); Isiah Joseph, Virginia Beach, VA (US); Gary Gordon, Suffolk, VA (US)

(*) Notice: Subject to any disclaimer, the term of this patent is extended or adjusted under 35 U.S.C. 154(b) by 327 days.

(21) Appl. No.: 16/812,790

(22) Filed: Mar. 9, 2020

(65) Prior Publication Data

US 2021/0145184 A1 May 20, 2021

Related U.S. Application Data

(60) Provisional application No. 62/936,454, filed on Nov. 16, 2019.

(51) Int. Cl.
*A47C 31/00* (2006.01)
*A61L 2/18* (2006.01)
*A61L 2/10* (2006.01)
*A47C 7/62* (2006.01)

(52) U.S. Cl.
CPC ............ *A47C 31/007* (2013.01); *A47C 7/62* (2013.01); *A61L 2/10* (2013.01); *A61L 2/18* (2013.01); *A61L 2202/11* (2013.01)

(58) Field of Classification Search
CPC .......... A61L 2/10; A61L 2/18; A61L 2202/11; A47C 7/62; A47C 31/007
See application file for complete search history.

(56) References Cited

U.S. PATENT DOCUMENTS

| 6,973,679 B1* | 12/2005 | Schad | E03D 9/085 |
| | | | 4/443 |
| 2007/0256226 A1* | 11/2007 | Pinizzotto | E03D 9/08 |
| | | | 4/420.4 |
| 2014/0137318 A1* | 5/2014 | Dorra | E03D 9/08 |
| | | | 4/233 |

FOREIGN PATENT DOCUMENTS

CN 206543063 U * 10/2017

OTHER PUBLICATIONS

English language machine translation of CN 206543063 U, Inventor: Li (Year: 2017).*

* cited by examiner

*Primary Examiner* — Sean E Conley
(74) *Attorney, Agent, or Firm* — William G. Sykes

(57) ABSTRACT

A self-sanitizing chair is shown and described. The chair may comprise a seating surface, legs, arm rest, head rest, and a sanitizing system. The latter may include a UV light source and a sanitizing fluid dispensing system. UV light and sanitizing fluid are applied to surfaces of the chair contacted by a human user. Indicating lights indicate when sanitizing is being performed, when sanitizing fluid is drying, and when the chair is ready for the next user. A control circuit operates the indicating lights and includes an occupant sensor. Sanitizing is inhibited in the presence of an occupant and commenced when the occupant has left the chair.

1 Claim, 4 Drawing Sheets

MODIFIED AND IMPROVED SELF-SANITIZING CHAIR

RELATED APPLICATIONS

This application claims priority in accordance with 37 CF.R. ¶1.19(e) to U.S. Provisional Patent Application Ser. No. 62/936,454 filed for MODIFIED AND IMPROVED SELF-SANITIZING CHAIR filed Nov. 16, 2019 which is included herein in its entirety by reference.

FIELD OF THE INVENTION

The present invention relates to chairs, and more particularly, to a chair having self-sanitizing features.

BACKGROUND OF THE INVENTION

Bacteria, viruses, and other pathogens are hazards to health, particularly in publicly used venues. Examples include waiting rooms, movie and stage and other indoor mass public seating, particularly those providing upholstered seating. In medical offices and hospitals, the hazards are all the greater since patrons are there for health related reasons, frequently bringing pathogens to the scene.

Efforts to minimize pathogenic contamination typically rely on spraying and/or fluid sanitizers onto affected furniture. While this approach is helpful, more needs to be done to bring the threat of pathogens under control. Exposure to fluid sanitizers may possibly be too brief to be fully effective. Also, effective use of fluid sanitizers depends on diligent application by sanitation personnel. Contaminated areas may be ignored inadvertently and inadequately sanitized for example.

There remains a need for improved self-sanitizing chairs.

SUMMARY OF THE INVENTION

The present invention provides a self-sanitizing chair which addresses the priorly noted concerns. To this end, the self-sanitizing chair may comprise a seating surface, legs, arm rest, head rest, and a sanitizing system. The latter may include a UV light source and optionally, a sanitizing fluid dispensing system. UV light and sanitizing fluid (if provided) are applied to surfaces of the chair contacted by a human user.

Indicating lights indicate when sanitizing is being performed, when sanitizing fluid (if provided) is drying, and when the chair is ready for the next user. A control circuit operates the indicating lights and includes an occupant sensor. Sanitizing is inhibited in the presence of an occupant and commenced when the occupant has left the chair.

The present invention provides improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
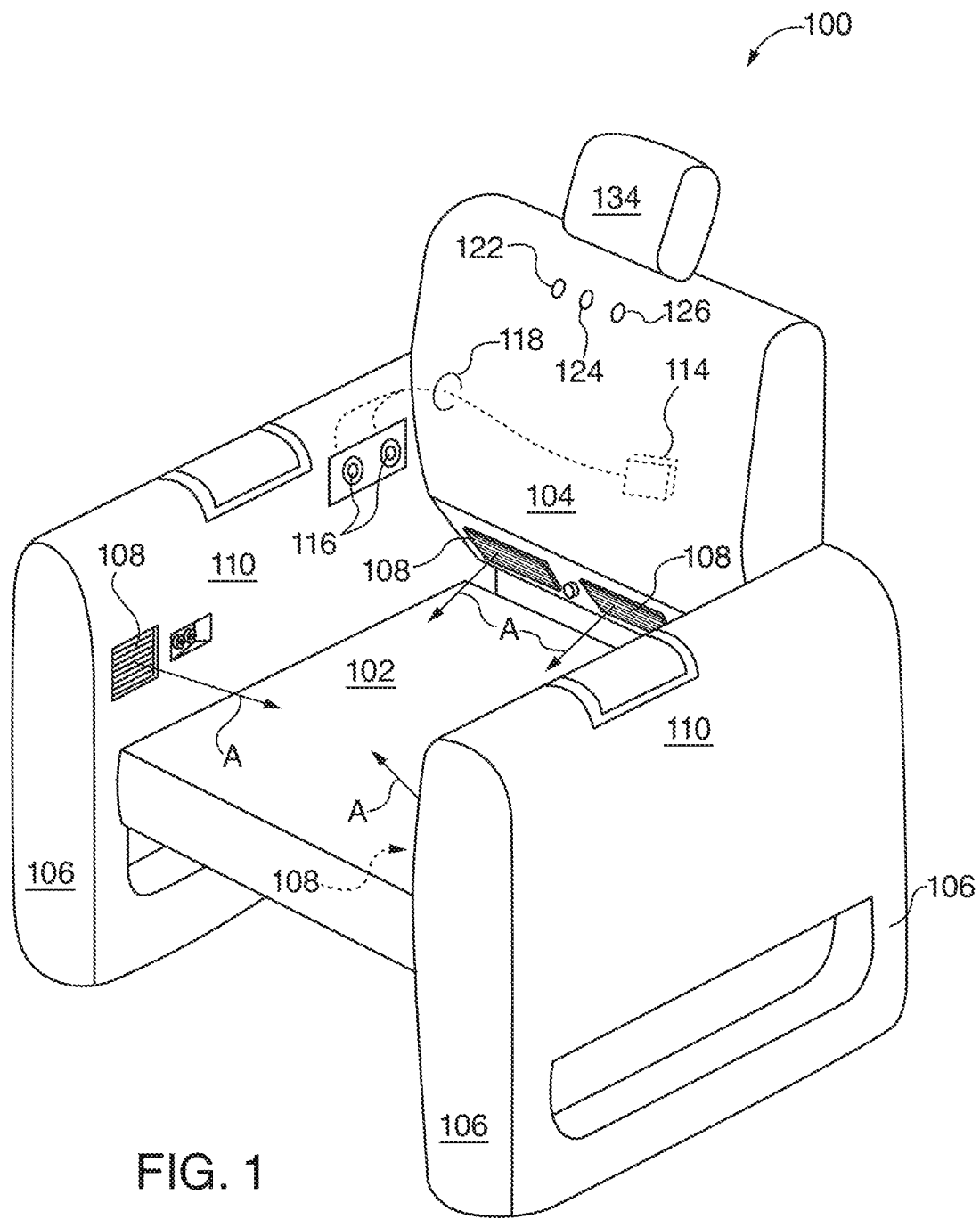
FIG. 1 is a front perspective view of one embodiment of a self-sanitizing chair, according to the invention.

Referring first to FIG. 1, according to a first embodiment of the invention, there is shown a self-sanitizing chair 100 comprising a seating surface 102, a seat back 104 abutting seating surface 102, and at least one leg 106. An ultraviolet (UV) emitting element 108 may be coupled to self-sanitizing chair 100 and oriented to project UV light (shown as arrows A) against at least one part of self-sanitizing chair 100 contacted by a person (not shown) sitting thereon. In the embodiment of FIG. 1, seating surface 102 may comprise a cushion horizontally supported on a frame (neither separately shown).

Emitted light is preferably in the ultraviolet band of frequencies, and more preferably, includes light in the UV-C band of frequencies.

It should be noted at this point that orientational terms such as vertical and horizontal refer to the subject drawing as viewed by an observer. The drawing figures depict their subject matter in orientations of normal use, which could obviously change with changes in posture and position of the novel accessory mount as mounted on the novel self-sanitizing chair. Therefore, orientational terms must be understood to provide semantic basis for purposes of description, and do not limit the invention or its component parts in any particular way.

In other embodiments (not shown), legs 106 may be plural, singular (e.g., centered relative to seating surface 102, this embodiment not being shown), or may take the form of a continuous skirt located for example along a perimeter of seating surface 102. In a further embodiment, any of seating surface 102, seat back 104, and leg(s) 106 may be integrated or alternatively described, may structurally or visually (or both) merge into one another. Illustratively, armrests 110 merge structurally and visually with legs 106. Self-sanitizing chair 100 may further comprise at least one armrest 110 coupled to self-sanitizing chair 100, wherein UV emitting element 108 may be arranged to project UV light against armrest 110 (to be described further hereinafter).

As seen in FIG. 1, seat back 104 may further comprises a headrest 134.

Figure 2:
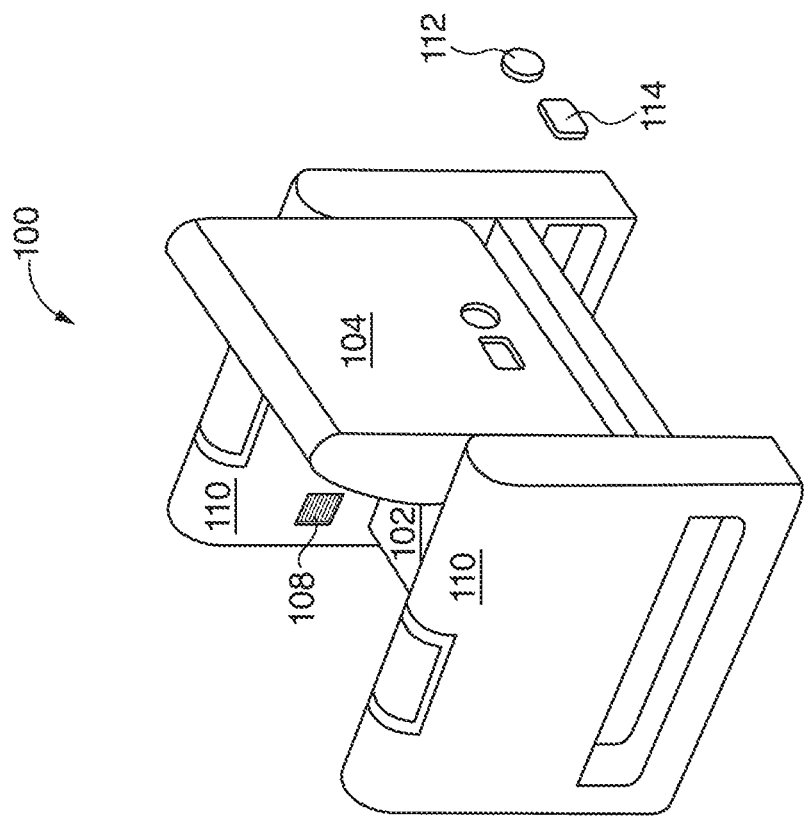
FIG. 2 is a rear perspective view of the embodiment of FIG. 1.
Figure 3:
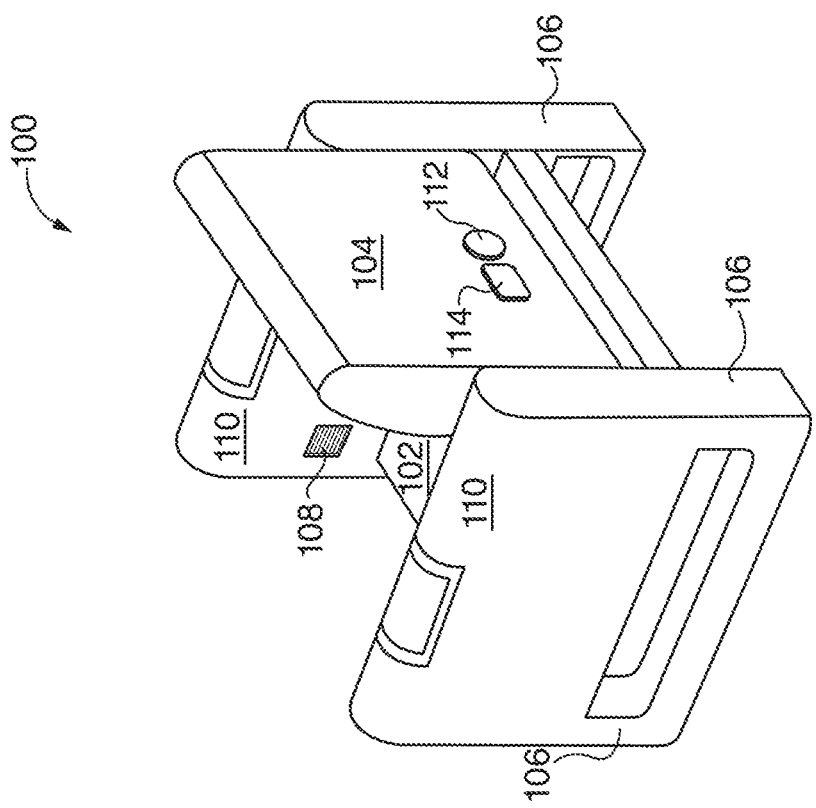
FIG. 3 is an exploded view of FIG. 2.

FIGS. 2 and 3 show self-sanitizing chair 100 of FIG. 1 from another view. Self-sanitizing chair of FIG. 1 may be battery powered. A battery 112 (shown in FIG. 4) may be enclosed within seat back 104 for example.

Figure 4:
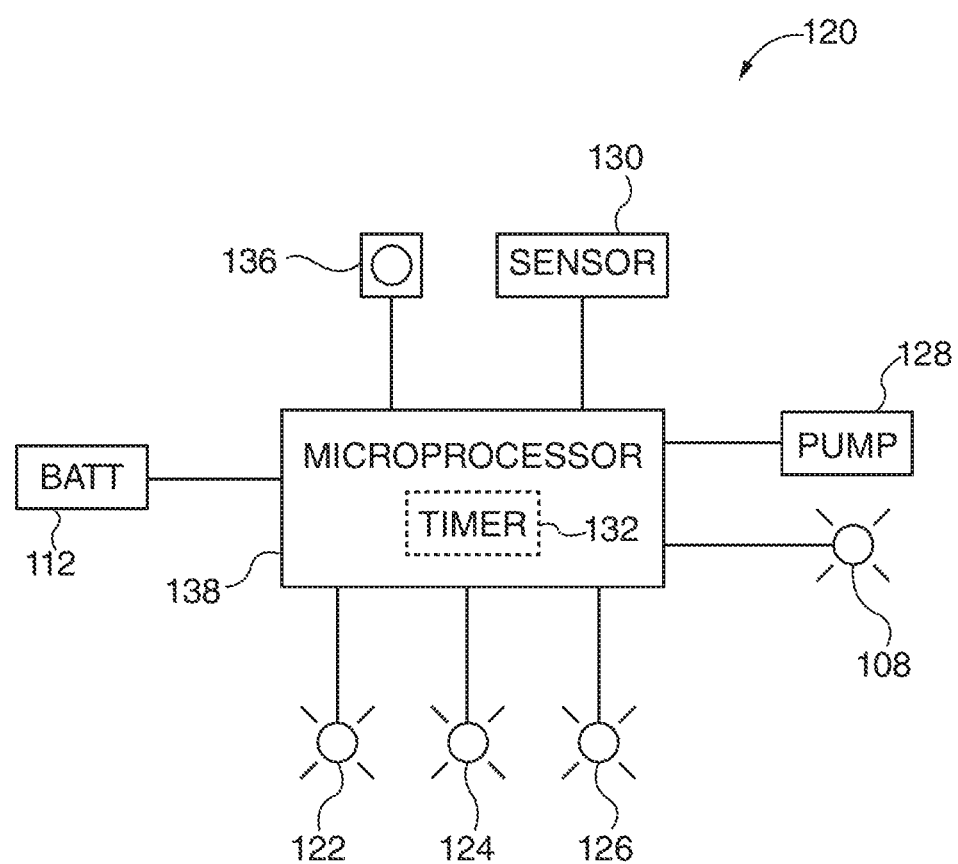
FIG. 4 is a diagrammatic illustration of an electrical power and control circuit usable to implement functions of embodiments of the self-sanitizing chair of the present invention.

Again referring to FIG. 1, self-sanitizing chair 100 may further comprise a fluid dispensing system for dispensing a sanitizing fluid onto the part of self-sanitizing chair 100 contacted by the person sitting thereon. The fluid dispensing system may comprise a reservoir 114 for storing the sanitizing fluid, a pressure source for pressurizing the sanitizing fluid, at least one nozzle 116 (see FIG. 1) for directing pressurized sanitizing fluid against the part of self-sanitizing chair 100 contacted by the person sitting thereon, and conduits 118 (FIG. 1) arranged to conduct sanitizing fluid from the pressure source to the at least one nozzle 116. In the embodiment of FIGS. 1-3, the pressure source comprises a gas spring maintaining the sanitizing fluid under pressure. The gas spring may be for example a pre-loaded charge of gas in reservoir 114. Alternatively, in self-sanitizing chair 100, the pressure source may comprise a pump 128. Pump 128 may be electrically powered, as shown in FIG. 4, or alternatively may comprise a hand pump 128.

Operating pressure for reservoir 114 may be obtained from hand pump 128 inside or otherwise part of reservoir 114, or serially within conduits 118 (these embodiments are not shown).

Some functions of self-sanitizing chair 100 may be automated, using electrical power for example. To this end, self-sanitizing chair 100 may further comprise a control circuit 120 (see FIG. 4) including a first status indicating lamp 122 arranged to indicate whether UV emitting element 108 is emitting UV light. In self-sanitizing chair 100, first status indicating lamp 122 may be arranged to indicate whether sanitizing is not being performed, whereby first status indicating lamp 122 indicates that self-sanitizing chair 100 is ready to receive a person desiring to sit thereon. In summary, where optional fluid dispensing and UV light are both used for sanitizing, first status indicating lamp 122 may signal that neither of these two sanitizing systems is operating, thereby resulting in a "ready" condition for accepting a new seat occupant.

Unless otherwise indicated, the terms "first", "second", etc., are used herein merely as labels, and are not intended to impose ordinal, positional, or hierarchical requirements on the items to which these terms refer. Moreover, reference to, e.g., a "second" item does not either require or preclude the existence of, e.g., a "first" or lower-numbered item, and/or, e.g., a "third" or higher-numbered item.

Control circuit 120 may further comprise a timer 132 (FIG. 4) arranged to measure a predetermined time period starting when pressurized sanitizing fluid ceases to be dispensed, and a third indicating lamp 126 for indicating that dispensed sanitizing fluid is drying, wherein the control circuit illuminates third indicating lamp 126 for the predetermined time period.

Control circuit 120 may include an occupancy sensor 130 arranged to sense whether a person is sitting on self-sanitizing chair 100. Control circuit 120 inhibits operation of UV emitting element 108 while the person is sitting on self-sanitizing chair 100. Self-sanitizing chair 100 may further comprise a second status indicating lamp 124 arranged to indicate that UV emitting element 108 has been operated (and operation has terminated) and that self-sanitizing chair 100 is ready to receive a new person desiring to sit thereon. Occupancy sensor 130 may comprise a switching arrangement such as spaced apart circuit members pressed into contact by the weight of a person, may comprise a proximity detector, may comprise a temperature detector, or may comprise a capacitance detector.

Control circuit 120 may be powered by battery 112, or alternatively, by suitable connection to an AC circuit, such as by plug and cord (not shown). If connected to the AC circuit, control circuit 120 will be understood to include all components necessary for operation as described, such as an AC-to-DC converter (not shown) regardless of whether explicitly described. It will further be appreciated that control circuit 120 may also take on functions of a power circuit in that connecting power may not only be a signal to operate, but also provide power necessary to operate.

Control circuit 120 may include a suitable controller for switching on and off, and optionally for selectively operating features of self-sanitizing chair 100. FIG. 4 depicts a manual pushbutton switch 136 arranged to turn on microprocessor 138, the latter managing functions described herein. Of course, control circuit 120 may be remotely controlled by a manual infrared signal emitter or by radio frequency apparatus (neither shown).

Figure 5:
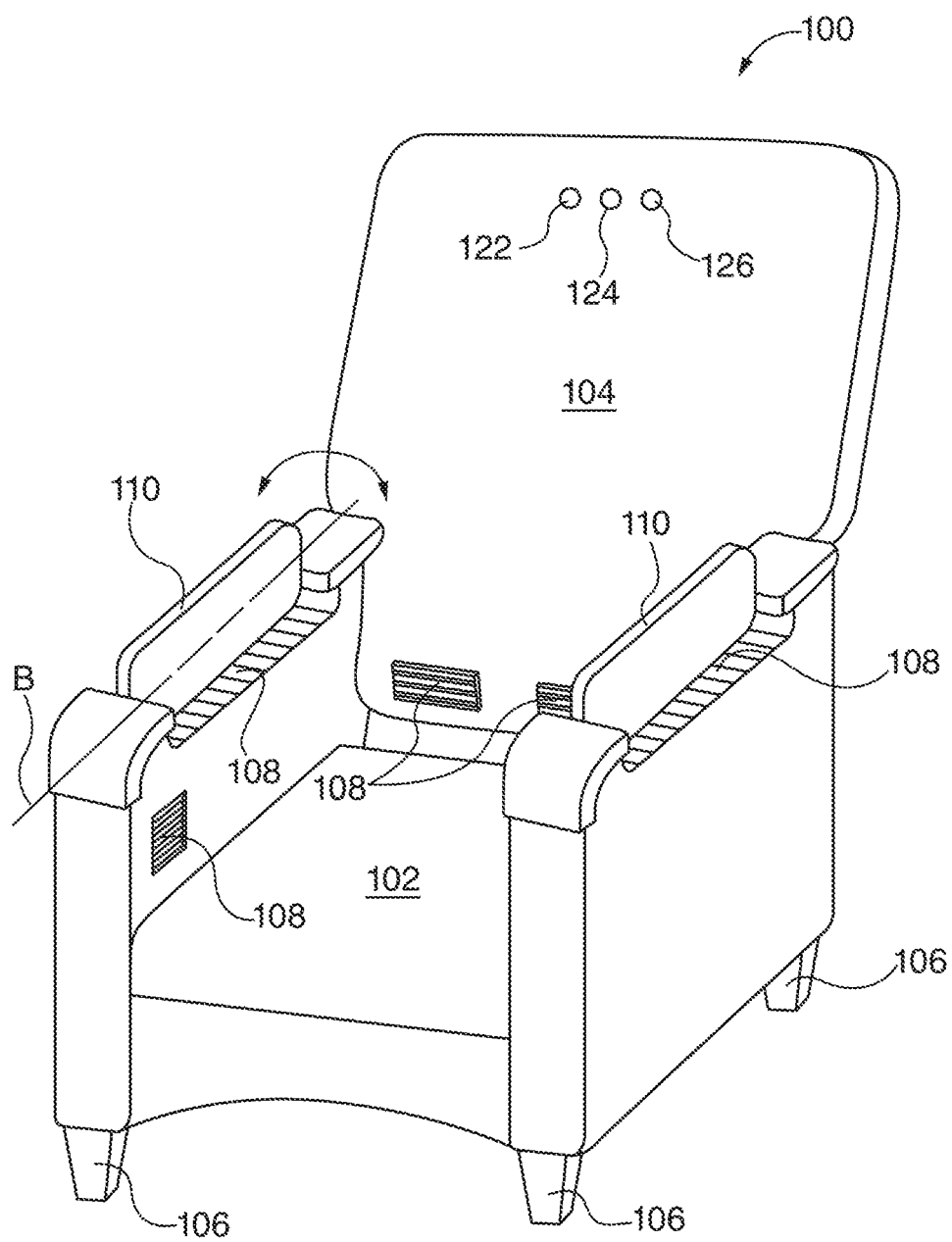
FIG. 5 is a front perspective view of a self-sanitizing chair 100 according to a further embodiment of the invention.

Turning now to FIG. 5, there is shown a further embodiment of self-sanitizing chair 100, wherein armrest 110 is movable to a deployed position suitable for supporting an arm of a person seated on self-sanitizing chair 100 (e.g., as shown in FIGS. 1-3) and a sanitizing position suitable for exposing a portion of armrest 110 contacted by the person seated on self-sanitizing chair 100 to UV light from the UV emitting element. Armrest 110 is pivotally mounted to rotate about an armrest axis B when moving between the deployed and sanitizing positions (the latter is depicted in FIG. 5).

For the purposes of this disclosure, a leg may be interpreted as any structure supporting the seating surface above a supporting environmental surface to enable a person to sit in self-sanitizing chair 100 with the person's leg or legs depending from the seating surface.

For the purposes of this disclosure, reference in the singular to UV light source may refer to only one UV light source or alternatively, to more than one UV light source. For example, it may be desired to provide a number of UV light sources in diverse locations to effectively direct emitted UV light against selected parts of the self-sanitizing chair 100, as depicted in FIGS. 1-3 and 5. Where provided, UV light sources, where plural, may be arranged to emit UV light simultaneously, or alternatively, to emit UV light in a pre-arranged sequence.

For the purposes of this disclosure, reference to indicator lamps in the plural may encompass using only one lamp, where that lamp is for example a three color (red-green-blue) light emitting diode (LED) controllable to produce any of the included colors in any desired combination. The visual result of such LEDs is that what appears to be one lamp can emit any desired color. Therefore, use of such a lamp may be exploited to eliminate necessity of providing separate lamps for providing each desired color.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

We claim:

1. A self-sanitizing chair, comprising:
    a seating surface, a seat back abutting the seating surface, the seat back further comprising a headrest, at least one armrest coupled to the self-sanitizing chair, wherein the armrest is movable to a deployed position suitable for supporting an arm of a person seated on the self-sanitizing chair and a sanitizing position suitable for exposing a portion of the armrest contacted by the person seated on the self-sanitizing chair to UV light from a UV emitting element, and at least one leg;
    a UV emitting element coupled to the self-sanitizing chair and oriented to project UV light against at least one part of the self-sanitizing chair contacted by a person sitting thereon, wherein the UV emitting element is arranged to project UV light against the armrest;

a fluid dispensing system for dispensing a sanitizing fluid onto the part of the self-sanitizing chair contacted by the person sitting thereon, wherein the fluid dispensing system comprises a reservoir for storing the sanitizing fluid, a pressure source for pressurizing the sanitizing fluid, at least one nozzle for directing pressurized sanitizing fluid against the part of the self-sanitizing chair contacted by the person sitting thereon, and conduits arranged to conduct sanitizing fluid from the pressure source to the at least one nozzle;

a control circuit including
- a timer arranged to measure a predetermined time period starting when pressurized santitizing fluid ceases to be dispensed,
- a first status indicating lamp arranged to indicate whether the UV emitting element is emitting UV light. a second status indicating lamp arranged to indicate that the UV emitting element has been operated and that the self-sanitizing chair is ready to receive a new person desiring to sit thereon, and a third indicating lamp for indicating that dispensed sanitizing fluid is drying, wherein the control circuit illuminates the third indicating lamp for the predetermined time period,
- an occupancy sensor arranged to sense whether a person is sitting on the self-sanitizing chair, and the control circuit inhibits operation of the UV emitting element and dispensing of the sanitary fluid while the person is sitting on the self-sanitizing chair.

* * * * *